(12) United States Patent
Mihara et al.

(10) Patent No.: US 6,335,177 B1
(45) Date of Patent: Jan. 1, 2002

(54) MICROORGANISMS AND METHOD FOR PRODUCING XYLITOL OR D-XYLULOSE

(75) Inventors: Yasuhiro Mihara; Sonoko Takeuchi; Yasuko Jojima; Naoto Tonouchi; Ryosuke Fudou; Kenzo Yokozeki, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/347,001

(22) Filed: Jul. 2, 1999

(30) Foreign Application Priority Data

| Jul. 8, 1998 | (JP) | .......................................... | 10-193472 |
| Oct. 30, 1998 | (JP) | .......................................... | 10-310398 |
| Jan. 20, 1999 | (JP) | .......................................... | 11-012244 |

(51) Int. Cl.$^7$ ............................ C12P 1/00; C12P 19/00; C12P 19/02; C12P 7/06; C12N 1/00
(52) U.S. Cl. ............................ 435/41; 435/72; 435/105; 435/161; 435/243; 435/252.1
(58) Field of Search ....................... 435/41, 156, 252.1, 435/161, 170, 105, 72, 243

(56) References Cited

U.S. PATENT DOCUMENTS 3,619,369 A  * 11/1971  Onishi et al. .................. 435/41
5,631,150 A  *  5/1997  Harkki et al. ................ 435/105

FOREIGN PATENT DOCUMENTS

WO     WO 94/10325       5/1994

OTHER PUBLICATIONS

Derwent Abstracts, AN Y14694, C. Boesch, et al., "Acetobacter Intermedius 16S rRNA Gene", Oct. 3, 1997.
Derwent Abstracts, AN X80775, M. Sievers, "G. Cerenus 16S rRNA Gene", Feb. 24, 1995.
Derwent Abstracts, AN 1972–27535T, JP 47 013707, Jul. 31, 1968.

* cited by examiner

Primary Examiner—Dave T. Nguyen
Assistant Examiner—Quang Nguyen
(74) Attorney, Agent, or Firm—Oblon, Spivak, McClelland, Maier & Neustadt, P.C.

(57) ABSTRACT

According to the present invention, there are provided microorganisms having an ability to producing xylitol or D-xylulose by fermentation, and a method for producing xylitol or D-xylulose using the microorganisms. Osmophilic microorganisms were collected from soil, and the obtained microorganisms were searched for a bacterium having an ability to produce xylitol or D-xylulose from glucose. Xylitol or D-xylulose is produced by culturing an isolated bacterium in a suitable medium to accumulate xylitol or D-xylulose in the medium, and collecting xylitol or D-xylulose from the medium.

7 Claims, 5 Drawing Sheets

```
S877  (SEQ ID NO: 2)    TGATCCTGGCTCAGAGCGAACGCTGGCGGCATGCTTAACACATGCAAGTCGCACGAACCT  60
S1009 (SEQ ID NO: 3)    ............................................................
S1019 (SEQ ID NO: 4)    ............................................................
S1023 (SEQ ID NO: 5)    ............................................................
P528  (SEQ ID NO: 1)    ....................................................G.......

S877    TTCGGGGGTTAGTGGCGGACGGGTGAGTAACGCGTAGGAACCTATCCAGAGGTGGGGGATA  120
S1009   ............................................................
S1019   ............................................................
S1023   .......................................T....................
P528    ........G...................G.T.......CG...................

S877    ACACCGGGAAACTGGTGCTAATACCGCATGATACCTGAGGGTTAAAGGCTTTTGTTGCCT  180
S1009   ............................................................
S1019   ............................................................
S1023   ....T.......................................C..............
P528    ....T.......................................C......GCGA..C....

S877    TTGGAGGGGCCTGCGTTTGATTAGCTAGTTGGTTGGGTAAAGGCTGACCAAGGCGATGAT  240
S1009   ............................................................
S1019   ............................................................
S1023   .A..........................................................
P528    G......A........C.........T......G..........CT..............

S877    CAATAGCTGGTTTGAGAGGATGATCAGCCACACTGGGACTGAGACACGGCCCAGACTCCT  300
S1009   ............................................................
S1019   ............................................................
S1023   ............................................................
P528    .G........C.................................................

S877    ACGGGAGGCAGCAGTGGGGAATATTGGACAATGGGGGCAACCCTGATCCAGCAATGCCGC  360
S1009   ............................................................
S1019   ............................................................
S1023   ............................................................
P528    .....................................C....G................
```

*FIG.2*

| | | |
|---|---|---|
| S877 | GTGTGTGAAGAAGGTCTTCGGATTGTAAAGCACTTTCACTAGGGAAGATGATGACGGTAC | 420 |
| S1009 | ............................................................ | |
| S1019 | ............................................................ | |
| S1023 | ............................................................ | |
| P528 | ........................GACG.....C.......... | |

| | | |
|---|---|---|
| S877 | CTAGAGAAGAAGCCCCGGCTAACTTCGTGCCAGCAGCCGCGGTAATACGAAGGGGGCTAG | 480 |
| S1009 | ............................................................ | |
| S1019 | ............................................................ | |
| S1023 | ............................................................ | |
| P528 | .CGT......................................... | |

| | | |
|---|---|---|
| S877 | CGTTGCTCGGAATGACTGGGCGTAAAGGGCGCGTAGGCGGTTTATACAGTCAGATGTGAA | 540 |
| S1009 | ............................................................ | |
| S1019 | ............................................................ | |
| S1023 | ............................................................ | |
| P528 | ......................T.........GT............. | |

| | | |
|---|---|---|
| S877 | ATCCCCGGGCTTAACCTGGGAACTGCATTTGATACGTATAGACTAGAGTCCGAGAGAGGA | 600 |
| S1009 | ............................................................ | |
| S1019 | ............................................................ | |
| S1023 | ............................................................ | |
| P528 | ..T..A.........T..GG.............GC.........GT.........G | |

| | | |
|---|---|---|
| S877 | TTGCGGAATTCCCAGTGTAGAGGTGAAATTCGTAGATATTGGGAAGAACACCAGTTGCGA | 660 |
| S1009 | ............................................................ | |
| S1019 | ............................................................ | |
| S1023 | ............................................................ | |
| P528 | ...T..........................................G..G... | |

| | | |
|---|---|---|
| S877 | AGGCGGCAATCTGGCTCGGAACTGACGCTGA | 691 |
| S1009 | ............................... | |
| S1019 | ............................... | |
| S1023 | ............................... | |
| P528 | .........C.......ATG......... | |

*FIG. 3*

SEQUENCE LISTING

```
<160> NUMBER OF SEQ ID NOS: 5

<210> SEQ ID NO 1
<211> LENGTH: 1438
<212> TYPE: DNA
<213> ORGANISM: Unknown Organism
<220> FEATURE:
<223> OTHER INFORMATION: Description of Unknown Organism:strain P528
<220> FEATURE:
<223> OTHER INFORMATION: N at position 1365 is A, T, G, or C

<400> SEQUENCE: 1
tgatcctggc tcagagcgaa cgctggcggc atgcttaaca catgcaagtc gcacggacct      60
ttcggggtga gtggcggacg ggtgagtaac gcgtagggat ctatccacgg gtgggggata    120
acactgggaa actggtgcta ataccgcatg atacctgagg gtcaaaggcg cgagtcgcct    180
gtggaggagc ctgcgttcga ttagcttgtt ggtgggtaa aggcctacca aggcgatgat    240
cgatagctgg tctgagagga tgatcagcca cactgggact gagacacggc ccagactcct    300
acgggaggca gcagtgggga atattggaca atgggcgcaa gcctgatcca gcaatgccgc    360
gtgtgtgaag aaggtcttcg gattgtaaag cactttcgac ggggacgatg atgacggtac    420
ccgtagaaga agccccggct aacttcgtgc cagcagccgc ggtaatacga aggggggctag    480 cgttgctcgg aatgactggg cgtaaagggc gtgtaggcgg ttgttacagt cagatgtgaa    540
attccagggc ttaaccttgg ggctgcattt gatacgtagc gactagagtg tgagagaggg    600
ttgtggaatt cccagtgtag aggtgaaatt cgtagatatt gggaagaaca ccggtggcga    660
aggcggcaac ctggctcatg actgacgctg aggcgcgaaa gcgtggggag caaacaggat    720
tagataccct ggtagtccac gctgtaaacg atgtgtgctg gatgttgggt aacttagtta    780
ctcagtgtcg aagctaacgc gctaagcaca ccgcctggga agtacggccg caaggttgaa    840
actcaaagga attgacgggg gcccgcacaa gcggtggagc atgtggttta attcgaagca    900
acgcgcagaa ccttaccagg gcttgacatg gggaggctgt actcagagat gggtatttcc    960
cgcaagggac ctcctgcaca ggtgctgcat ggctgtcgtc agctcgtgtc gtgagatgtt   1020
gggttaagtc ccgcaacgag cgcaaccctc gcctttagtt gccagcacgt ttgggtgggc   1080
actctagagg aactgccggt gacaagccgg aggaaggtgg ggatgacgtc aagtcctcat   1140
ggcccttatg tcctgggcta cacacgtgct acaatggcgg tgacagtggg aagctagatg   1200
gtgacatcat gccgatctca aaaagccgtc tcagttcgga ttgtactctg caactcgagt   1260
acatgaaggt ggaatcgcta gtaatcgcgg atcagcatgc cgcggtgaat acgttcccgg   1320
gccttgtaca caccgcccgt cacaccatgg gagttggttt gaccngaagc cggtgagcga   1380
accgcaagga cgcagccgac cacggtcggg tcagcgactg gggtgaagtc gtaacaag     1438

<210> SEQ ID NO 2
<211> LENGTH: 1436
<212> TYPE: DNA
<213> ORGANISM: Unknown Organism
```

-continued

```
<220> FEATURE:
<223> OTHER INFORMATION: Description of Unknown Organism:strain S877

<400> SEQUENCE: 2
tgatcctggc tcagagcgaa cgctggcggc atgcttaaca catgcaagtc gcacgaacct      60
ttcggggtta gtggcggacg ggtgagtaac gcgtaggaac ctatccagag gtgggggata     120
acaccgggaa actggtgcta ataccgcatg ataccgaggg gttaaaggct tttgttgcct     180 ttggagggc ctgcgtttga ttagctagtt ggttgggtaa aggctgacca aggcgatgat     240
caatagctgg tttgagagga tgatcagcca cactgggact gagacacggc ccagactcct     300
acgggaggca gcagtgggga atattggaca atgggggcaa ccctgatcca gcaatgccgc     360
gtgtgtgaag aaggtcttcg gattgtaaag cactttcact agggaagatg atgacggtac     420
ctagagaaga agccccggct aacttcgtgc cagcagccgc ggtaatacga agggggctag     480
cgttgctcgg aatgactggg cgtaaagggc gcgtaggcgg tttatacagt cagatgtgaa     540 atccccggc ttaacctggg aactgcattt gatacgtata gactagagtc gagagagga     600 ttgcggaatt cccagtgtag aggtgaaatt cgtagatatt gggaagaaca ccagttgcga     660
aggcggcaat ctggctcgga actgacgctg aggcgcgaaa gcgtggggag cgaacaggat     720
tagataccct ggtagtccac gctgtaaacg atgtgtgctg gatgttggga aacttagttt     780
ttcagtgtcg aagctaacgt gttaagcaca ccgcctgggg agtacgaccg caaggttgaa     840
actcaaagaa attgacgggg gcccgcacaa gcggtggagc atgtggttta attcgaagca     900
acgcgcagaa ccttaccagg tcttgtatgg ggaggacgtg ctcagagatg agtatttctt     960
cggacctccc gcacaggtgc tgcatggctg tcgtcagctc gtgtcgtgag atgttgggtt    1020
aagtcccgca acgagcgcaa ccctgtctt tagttgccat cacgtttggg tgggcactct    1080
agagagactg ccggtgacaa gccggaggaa ggtggggatg acgtcaagtc ctcatggccc    1140
ttatgacctg ggctacacac gtgctacaat ggcggtgaca atgggaagct acatggtgac    1200
atgatgccga tctcaaaaaa ccgtctcagt tcggattgca ctctgcaact cgagtgcatg    1260
aaggtggaat cgctagtaat cgtggatcag catgccacgg tgaatacgtt cccgggcctt    1320
gtacacaccg cccgtcacac catgggagtt ggtttgacct taagccggtg agcgaaccgc    1380
aagggcgcag cgacccacgg tcgggtcagc gactggggtg aagtcgtaac aaggta        1436

<210> SEQ ID NO 3
<211> LENGTH: 691
<212> TYPE: DNA
<213> ORGANISM: Unknown Organism
<220> FEATURE:
<223> OTHER INFORMATION: Description of Unknown Organism:strain S1009

<400> SEQUENCE: 3
tgatcctggc tcagagcgaa cgctggcggc atgcttaaca catgcaagtc gcacgaacct      60
ttcggggtta gtggcggacg ggtgagtaac gcgtaggaac ctatccagag gtgggggata     120
acaccgggaa actggtgcta ataccgcatg ataccgaggg gttaaaggct tttgttgcct     180 ttggagggc ctgcgtttga ttagctagtt ggttgggtaa aggctgacca aggcgatgat     240
caatagctgg tttgagagga tgatcagcca cactgggact gagacacggc ccagactcct     300
acgggaggca gcagtgggga atattggaca atgggggcaa ccctgatcca gcaatgccgc     360
gtgtgtgaag aaggtcttcg gattgtaaag cactttcact agggaagatg atgacggtac     420
ctagagaaga agccccggct aacttcgtgc cagcagccgc ggtaatacga agggggctag     480
```

```
cgttgctcgg aatgactggg cgtaaagggc gcgtaggcgg tttatacagt cagatgtgaa     540
atccccgggc ttaacctggg aactgcattt gatacgtata gactagagtc cgagagagga     600
ttgcggaatt cccagtgtag aggtgaaatt cgtagatatt gggaagaaca ccagttgcga     660
aggcggcaat ctggctcgga actgacgctg a                                    691
```

<210> SEQ ID NO 4
<211> LENGTH: 691
<212> TYPE: DNA
<213> ORGANISM: Unknown Organism
<220> FEATURE:
<223> OTHER INFORMATION: Description of Unknown Organism:strain S1019

<400> SEQUENCE: 4

```
tgatcctggc tcagagcgaa cgctggcggc atgcttaaca catgcaagtc gcacgaacct     60
ttcggggtta gtggcggacg ggtgagtaac gcgtaggaac ctatccagag gtgggggata    120
acaccgggaa actggtgcta ataccgcatg atacctgagg gttaaaggct tttgttgcct    180
ttggaggggc ctgcgtttga ttagctagtt ggttgggtaa aggctgacca aggcgatgat    240
caatagctgg tttgagagga tgatcagcca cactgggact gagacacggc ccagactcct    300 acggaggca gcagtgggga atattggaca atggggcaa ccctgatcca gcaatgccgc     360
gtgtgtgaag aagtcttcg gattgtaaag cactttcact agggaagatg atgacggtac    420
ctagagaaga agccccggct aacttcgtgc cagcagccgc ggtaatacga aggggctag     480 cgttgctcgg aatgactggg cgtaaagggc gcgtaggcgg tttatacagt cagatgtgaa    540
atccccgggc ttaacctggg aactgcattt gatacgtata gactagagtc cgagagagga    600
ttgcggaatt cccagtgtag aggtgaaatt cgtagatatt gggaagaaca ccagttgcga    660
aggcggcaat ctggctcgga actgacgctg a                                   691
```

<210> SEQ ID NO 5
<211> LENGTH: 691
<212> TYPE: DNA
<213> ORGANISM: Unknown Organism
<220> FEATURE:
<223> OTHER INFORMATION: Description of Unknown Organism:strain S1023

<400> SEQUENCE: 5

```
tgatcctggc tcagagcgaa cgctggcggc atgcttaaca catgcaagtc gcacgaacct     60
ttcggggtta gtggcggacg ggtgagtaac gcgtaggaac ctatcctgag gtgggggata    120
acactgggaa actggtgcta ataccgcatg atacctgagg gtcaaaggct tttgttgcct    180
taggaggggc ctgcgtttga ttagctagtt ggttgggtaa aggctgacca aggcgatgat    240
caatagctgg tttgagagga tgatcagcca cactgggact gagacacggc ccagactcct    300 acggaggca gcagtgggga atattggaca atggggcaa ccctgatcca gcaatgccgc     360
gtgtgtgaag aagtcttcg gattgtaaag cactttcact agggaagatg atgacggtac    420
ctagagaaga agccccggct aacttcgtgc cagcagccgc ggtaatacga aggggctag     480 cgttgctcgg aatgactggg cgtaaagggc gcgtaggcgg tttatacagt cagatgtgaa    540
atccccgggc ttaacctggg aactgcattt gatacgtata gactagagtc cgagagagga    600
ttgcggaatt cccagtgtag aggtgaaatt cgtagatatt gggaagaaca ccagttgcga    660
aggcggcaat ctggctcgga actgacgctg a                                   691
```

MICROORGANISMS AND METHOD FOR PRODUCING XYLITOL OR D-XYLULOSE

TECHNICAL FIELD

The present invention relates to novel microorganisms having an ability to produce xylitol or D-xylulose, and a method for producing xylitol or D-xylulose by using a microorganism having an ability to produce xylitol or D-xylulose. D-Xylulose is useful as a material for the production of xylitol, and xylitol is useful as a sweetener in the field of food industry and the like.

BACKGROUND ART

The demand of xylitol which is a naturally occurring sugar alcohol is expected to increase in future. Xylitol is a promising low-calorie sweetener because it has lower calories and exhibits comparable sweetness compared with sucrose. In addition, because of its anti-dental caries property, it is utilized as a dental caries preventive sweetener. Furthermore, because xylitol does not elevate glucose level, it is utilized for fluid therapy in the treatment of diabetes. For these reasons, it is expected that the demand of xylitol will increase in future.

The current industrial production of xylitol mainly relies on hydrogenation of D-xylose as disclosed in U.S. Pat. No. 4,008,285. D-Xylose used as a raw material is obtained by hydrolysis of plant materials such as trees, straws, corn cobs, oat hulls and other xylan-rich materials.

However, such D-xylose produced by hydrolysis of plant materials suffers a drawback that it is rather expensive, and it is arisen from high production cost. For example, the low yield of the hydrolysis treatment of plant materials leads to low purity of the produced D-xylitol. Therefore, the acid used for the hydrolysis and the dyes must be removed by ion exchange treatment after the hydrolysis treatment, and the resulting D-xylose must be further crystallized to remove other hemicellulosic saccharides. In order to obtain D-xylose suitable for foodstuffs, further purification would be required. Such ion exchange treatment and crystallization treatment invite the increase of production cost.

Therefore, several methods for producing xylitol have been developed, which utilize readily available raw materials and generate little waste. For example, there have been developed methods for producing xylitol utilizing other pentitols as a starting material. One of such readily available pentitols is D-arabitol, and D-arabitol can be produced by using yeast (*Can. J. Microbiol.*, 31, 1985, 467–471; *J. Gen. Microbiol.*, 139, 1993, 1047–54). As a method for producing xylitol by utilizing D-arabitol as a raw material, there can be mentioned the method reported in *Applied Microbiology.*, 18, 1969, 1031–1035, which comprises producing D-arabitol from glucose by fermentation using *Debaryomyces hansenii* ATCC20121, then converting the D-arabitol into D-xylulose using *Acetobacter suboxydance*, and converting D-xylulose into xylitol by the action of *Candida guilliermondii* var. *soya*.

EP 403 392A and EP421 882A disclose methods comprising producing D-arabitol by fermentation using an osmosis-resistant yeast, then converting D-arabitol into D-xylulose using a bacterium belonging to the genus Acetobacter, the genus Gluconobacter, or the genus Klebsiella, forming a mixture of xylose and D-xylulose from the D-xylulose by the action of glucose (xylose) isomerase, and converting the obtained mixture of xylose and D-xylulose into xylitol by hydrogenation. There is also disclosed the production of xylitol comprising preliminarily concentrating xylose in the mixture of xylose and D-xylulose and converting the xylose into xylitol by hydrogenation.

However, those methods for the production of xylitol mentioned above utilize D-arabitol produced by fermentation as a starting material, and convert it by multiple process steps. Therefore, the processes are complicated, and less satisfactory ones in view of process economy compared with the methods based on extraction.

Accordingly, there has been desired a microorganism which has an ability to produce xylitol or D-xylulose through a single step by fermentation starting from glucose as used in the production of other saccharides and sugar alcohols. However, such a bacterium having an ability to produce xylitol or D-xylulose has not been reported so far.

On the other hand, breeding of xylitol fermenting bacteria has been attempted by using gene manipulation techniques. International Publication W094/10325 discloses production of xylitol from glucose by fermentation by using a recombinant microorganism obtained by introducing an arabitol dehydrogenase gene derived from a bacterium belonging to the genus Klebsiella and a xylitol dehydrogenase gene derived from a bacterium belonging to the genus Pichia into an arabitol fermenting microorganism (yeast belonging to the genus Candida, the gunus Torulopsis, or the genus Zygosaccharomyces). However, while production of 15 g/L of xylitol from 400 g/L of glucose has been reported for the aforementioned recombinant microorganism, it does not reach a practically useful accumulation level. Moreover, the aforementioned recombinant microorganism is introduced with a gene derived from a different species, and therefore information about its safety cannot be considered sufficient.

SUMMARY OF THE INVENTION

The present invention has been accomplished in view of the aforementioned state of the art, and its object is to provide a microorganism having an ability to produce xylitol or D-xylulose from glucose by fermentation, as well as a method for producing xylitol or D-xylulose utilizing such a microorganism.

In order to achieve the aforementioned object, the present inventors searched a microorganism having an ability to produce xylitol or D-xylulose from glucose by fermentation. As for direct production of sugar alcohols by fermentation of microorganisms such as yeasts, there have also been reported production of glycerol by using *Zygosaccharomyces acidifaciens* (*Arch. Biochem.*, 7, 257–271 (1945)), production of erythritol by using a yeast belonging to the genus Trychosporonoides (Trychosporonoides sp., *Biotechnology Letters*, 15, 240–246 (1964)) and the like, in addition to the aforementioned arabitol fermentation. All of these yeasts having sugar alcohol producing ability show osmophilicity, i.e., good growth in a culture medium of high osmotic pressure. Therefore, while any microbes having xylitol producing ability have not found among the osmophilic yeasts, the present inventors considered that a novel microorganism having xylitol producing ability may exist among osmophilic microorganisms, and extensively screened osmophilic microorganisms. As a result, they found microorganisms having an ability to produce xylitol and D-xylulose from glucose among osmophilic microorganisms. Those microorganisms were estimated to be novel bacteria from the viewpoint of taxonomic phylogeny based on the nucleotide sequence of 16S rRNA gene. The present invention has been accomplished based on the aforementioned finding.

Accordingly, the present invention provides a microorganism belonging to the family Acetobacteracea, which has a 16S rRNA gene comprising a nucleotide sequence of SEQ ID NO: 1 or a nucleotide sequence equivalent to the nucleotide sequence of SEQ ID NO: 1 from the viewpoint of molecular taxonomy based on the 16S rRNA sequence, and has an ability to produce xylitol or D-xylulose from glucose, and A microorganism which has a 16S rRNA gene comprising a nucleotide sequence of SEQ ID NO: 2 or a nucleotide sequence of SEQ ID NO: 2 equivalent to the nucleotide sequence from the viewpoint of molecular taxonomy based on the 16S rRNA sequence, and has an ability to produce xylitol or D-xylulose from glucose.

Examples of the aforementioned microorganisms include, for example, those microorganisms belonging to the genus Asaia or the genus Zucharibacter, more specifically strains of *Asaia ethanolifaciens* or *Zucharibacter floricola*. *Asaia ethanolifaciens* is a new species (sp. nov.) provisionally designated by the present inventors. The genus Zucharibacter and *Zucharibacter floricola* are a new genus (gen. nov.) and new species, respectively, which were provisionally designated by the present inventors.

Particular examples of the aforememtioned microorganisms include, for example, strain P528 (FERM BP-6751), strain S877 (EERM BP-6752), strain S1009 (FERM BP-6753), strain S1019 (FERM BP-6754), and strain S1023 (FERM BP-6755).

The 16S rRNA gene of the strain P528 comprises the nucleotide sequence of SEQ ID NO: 1, and the 16S rRNA gene of the strain S877 comprises the nucleotide sequence of SEQ ID NO: 2. Partial sequences of the 16S rRNA gene of the strains S1009, S1019, and S1023 are of SEQ ID NOS: 3–5, respectively. These nucleotide sequences are equivalent to the nucleotide sequence of SEQ ID NO: 2 from the viewpoint of molecular taxonomy based on the nucleotide sequence of the 16S rRNA.

The present invention also provides a method for producing xylitol or D-xylulose, which comprises culturing a microorganism having an ability to produce xylitol or D-xylulose from glucose in a suitable medium to accumulate xylitol or D-xylulose in the medium, and collecting xylitol or D-xylulose from the medium.

Examples of the microorganism used for the above method includes, for example, a microorganism belonging to the family Acetobacteracea, which has a 16S rRNA gene comprising a nucleotide sequence of SEQ ID NO: 1 or a nucleotide sequence equivalent to the nucleotide sequence from the viewpoint of molecular taxonomy based on the 16S rRNA sequence, and has an ability to produce xylitol or D-xylulose from glucose, and a microorganism belonging to the family Acetobacteracea, which has a 16S rRNA gene comprising a nucleotide sequence of SEQ ID NO: 2 or a nucleotide sequence equivalent to the nucleotide sequence from the viewpoint of molecular taxonomy based on the 16S rRNA sequence, and has an ability to produce xylitol or D-xylulose from glucose.

Specific examples of the aforementioned microorganisms include, for example, those microorganisms belonging to the genus Asaia or the genus Zucharibacter, more specifically strains of *Asaia ethanolifaciens* or *Zucharibacter floricola*. Particular examples of the aforementioned microorganisms include, for example, the strains P528, S877, S1009, S1019, and S1023.

The present invention further provides a method for producing ethanol, which comprises culturing the microbial strain P528 (FERM BP-6751) in a suitable medium to accumulate ethanol in the medium, and collecting ethanol from the medium.

According to the present invention, xylitol or D-xylulose can be efficiently produced from inexpensive materials such as glucose.

Further, ethanol can be produced by using the strain P528.

BRIEF DESCRIPTION OF THE DRAWINGS

FIG. 2 shows alignment of partial sequences of 16S rRNA of xylitol producing microorganisms. It shows comparison of nucleotide sequences of nucleotide numbers 1–691 of SEQ ID NO: 1 and SEQ ID NO: 2 and the nucleotide sequences of SEQ ID NOS: 3–5. The dots (·) indicate common nucleotides.

FIG. 3 is continuance of FIG. 2.

DETAILED DESCRIPTION OF THE INVENTION

Figure 1:
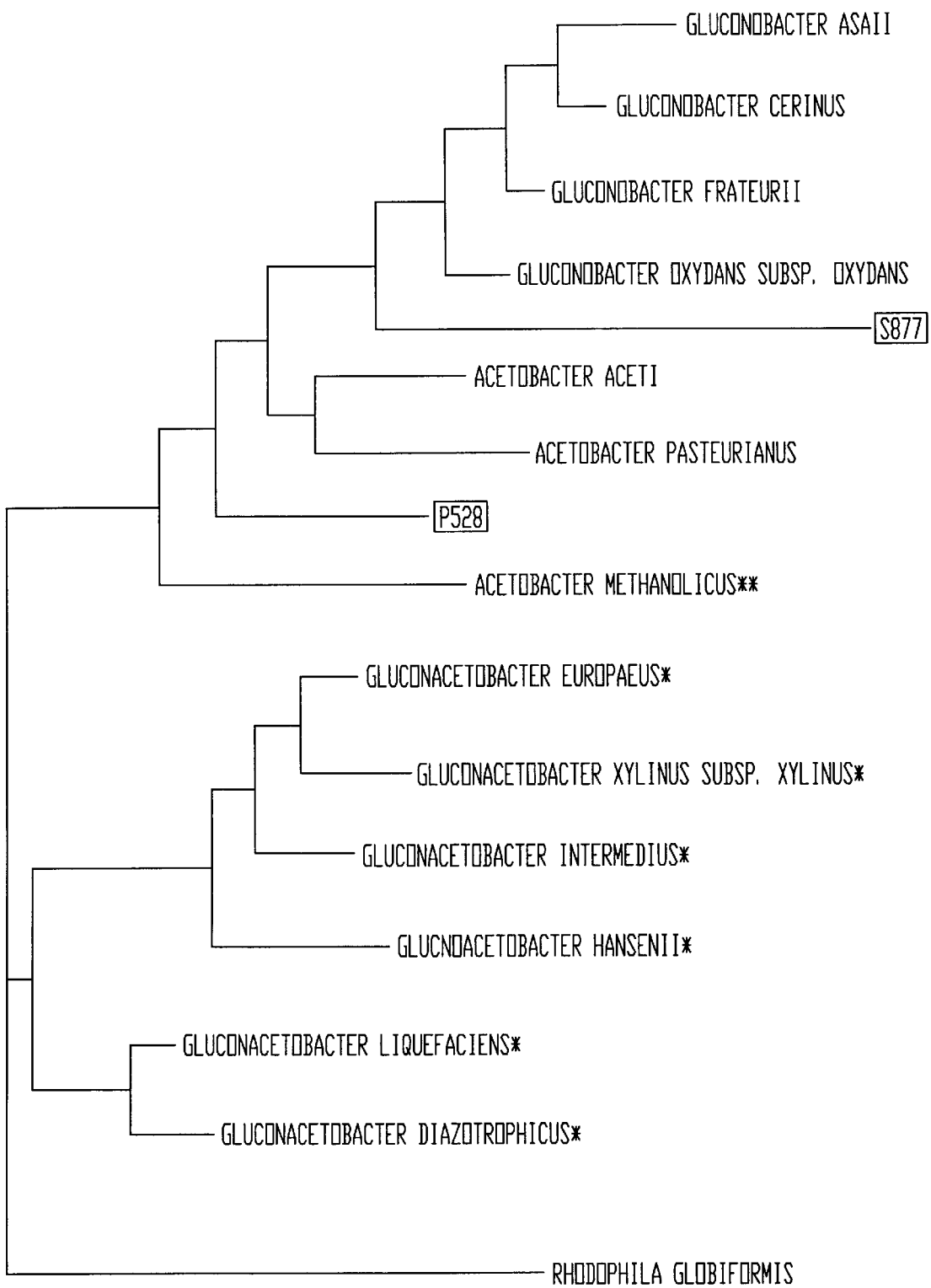
FIG. 1 shows a molecular phylogenetic tree of the microorganisms of the present invention and analogous bacteria based on the nucleotide sequences of 16S rRNA.

The present invention will be explained in detail hereinafter.

<1> Microorganisms of the Present Invention

The present inventors extensively screened osmophilic microorganisms as described in examples mentioned hereinafer, and as a result, found novel microorganisms having an ability to produce xylitol or D-xylulose from glucose. Those microorganisms were designated as strains P528, S877, S1009, S1019, and S1023.

Microbiological characteristics of the above strains will be mentioned below.

[1] Morphological and Cultural Characteristics

The aforementioned strains were cultured in YM medium (1% glucose, 0.5% peptone, 0.3% yeast extract, 0.3% malt extract, pH 6.0) supplemented with 11% (w/v) D-glucose at 30° C. for 3 days, and then observed by a microscope. The results are shown in Table 1.

TABLE 1

| Strain | P528 | S877 | S1009 | S1019 | S1023 |
|---|---|---|---|---|---|
| Cell size | 0.8–1 μm × 4.5 . 5 μm | 0.8–1 μm × 2.5–3 μm | 0.8–1 μm × 2.5–3 μm | 0.8–1 μm × 2.5–4 μm | 0.8–1 μm × 2–2.5 μm |
| Shape | Rod | Rod | Rod | Rod | Rod |
| Motility | None | None | None | None | None |
| Spore | None | None | None | None | None |

[2] Cultural Characteristics (1) Agar Plate Culture

The strains were cultured on YM culture plates supplemented with 11% (w/v) D-glucose at 30° C. for 3 days, and observed characteristics are shown in Table 2.

TABLE 2

| Strain | P528 | S877 | S1009 | S1019 | S1023 |
|---|---|---|---|---|---|
| Growth | Good | Good | Good | Good | Good |
| Colony | Round, smooth for entire periphery | Round, smooth for entire periphery | Round, smooth for entire periphery | Round, smooth for entire periphery | Round, smooth for entire periphery |
| Surface | Low convex | Low convex | Low convex | Convex | Low convex |
| Glisten | Lipid-like glisten | Lipid-like glisten | Lipid-like glisten | Lipid-like glisten | Lipid-like glisten |
| Color | Lemon yellow | Slightly yellow | Slightly yellow | Slightly yellow | Slightly yellow |

(2) Broth Culture

The strains were cultured in YM culture broth supplemented with 11% (w/v) D-glucose at 30° C. for 3 days, and observed characteristics are shown in Table 3.

TABLE 3

| Strain | P528 | S877 | S1009 | S1019 | S1023 |
|---|---|---|---|---|---|
| Surface growth | None | None | None | None | None |
| Turbidity | Strongly turbid | Strongly turbid | Strongly turbid | Strongly turbid | Strongly turbid |
| Precipitates | Lot of precipitates | Lot of precipitates | Lot of precipitates | Lot of precipitates | Lot of precipitates |

[3] Physiological Characteristics (1) Test Results for Various Physiological Characteristics are Shown in Table 4.

TABLE 4

| Strain | P528 | S877 | S1009 | S1019 | S1023 |
|---|---|---|---|---|---|
| Gram strain | Negative | Negative | Negative | Negative | Negative |
| Indole production | Negative | Negative | Negative | Negative | Negative |
| Hydrogen disulfide production | Negative | Negative | Negative | Negative | Negative |
| Oxidase | Negative | Negative | Negative | Negative | Negative |
| Catalase | Positive | Positive | Positive | Positive | Positive |
| O-F test | Positive | Negative | Negative | Negative | Negative |

(2) Optimum Growth Condition

Optimum growth temperature and optimum pH when the strains were cultured with the YM medium supplemented with 11% (w/v) D-glucose are shown in Table 5.

TABLE 5

| Strain | P528 | S877 | S1009 | S1019 | S1023 |
|---|---|---|---|---|---|
| Optimum growth temperature | 30° C. | 27° C. | 27° C. | 27° C. | 27° C. |
| Optimum growth pH | 5.0–7.0 | 5.0–7.0 | 5.0–7.0 | 5.0–7.0 | 5.0–7.0 |

(3) Growth Condition

Conditions which allow growth when the strains were cultured with the YM medium supplemented with 11% (w/v) D-glucose are shown in Table 6.

TABLE 6

| Strain | P528 | S877 | S1009 | S1019 | S1023 |
|---|---|---|---|---|---|
| Growth temperature | 10–37° C. | 10–37° C. | 10–32° C. | 10–32° C. | 10–32° C. |
| Growth pH | 2.5–9.0 | 2.5–9.0 | 2.5–9.0 | 2.5–9.0 | 2.5–9.0 |

(4) Optimum sucrose concentrations when the strains were cultured with the YM medium supplemented with sucrose are shown in Table 7.

TABLE 7

| Strain | P528 | S877 | S1009 | S1019 | S1023 |
|---|---|---|---|---|---|
| Optimum sucrose concentration | 20% | 10% | 10% | 10% | 10% |

(5) The strains were cultured in a medium containing 20% (w/v) D-glucose, 0.1% urea, and 0.5% yeast extract at 30° C. for 5 days. Saccharides detected in the medium after the cultivation are mentioned in Table 8.

TABLE 8

| Strain | P52B | SB77 | S1009 | S1019 | S1023 |
|---|---|---|---|---|---|
| Metabolite from glucose | Xylitol, D-xylulose, D-arabitol, sorbitol | Xylitol, D-xylulose, D-arabitol | Xylitol, D-xylulose, D-arabitol | Xylitol, D-xylulose, D-arabitol | Xylitol, D-xylulose, D-arabitol |

Among the aforementioned strains, four of the strains S877, S1009, S1019 and S1023 exhibit obligate osmophilicity, i.e., they can grow only in a medium added with a saccharide at a high concentration.

The major characteristic of those five microbial strains is the ability to produce xylitol or D-xylulose from glucose. Since any microorganism producing xylitol or D-xylulose from glucose has not been reported at all to date, the strains having such microbiological characteristics as mentioned above were determined to be novel microorganisms.

[4] Molecular Taxonomic Analysis

In order to determine taxonomic positions of the strains P528, S877, S1009, S1019 and S1023, nucleotide sequences of the 16S rRNA gene of these strains were determined and a molecular phylogenetic tree was prepared using those nucleotide sequences together with nucleotide sequences of 16S rRNA gene of closest microorganisms (FIG. 1). As a result, there has been suggested a possibility that the strain P528 belongs to the family Acetobacteracea, and is a new species belonging to the genus Acetobacter or a new genus analogous to the genus Acetobacter. On the other hand, there has been suggested a possibility that the strain S877 belongs to the family Acetobacteracea, and is a microorganism belonging to a new genus analogous to the genus Acetobacter or the genus Gluconobacter. Three of the strains S1009, S1019 and S1023 are considered to be the same species as the strain S877.

A method for studying evolution of organisms or genes based on a molecular phylogenetic tree has been established as molecular taxonomy (see, for example, "Bunshi Shinkagaku Nyumon (Introduction of Evolutionary Molecular Biology)", Section 7, Method for Preparation of Molecular Phylogenetic Tree and Evaluation thereof, Ed. by T. Kimura, Baifukan, Japan, pp. 164–184).

A molecular phylogenetic tree based on the nucleotide sequences of the 16S rRNA gene can be obtained by preparing a phylogenetic tree based on data obtained through multiple sequence alignment and calculation of evolution distance using nucleotide sequences of the 16S rRNA gene of a microorganism of interest together with those of known microorganisms estimated to be of the same species or analogous to the microorganism of interest. The nucleotide sequences of the 16S rRNA gene of known microorganisms used for the preparation of the molecular phylogenetic tree can be obtained by, for example, searching of available databases based on homology. The term "evolution distance" herein used means a total number of mutations per genetic locus (sequence length) for a certain gene.

The multiple sequence alignment and evolution distance calculation can be performed by, for example, using a commercially available software such as CLUSTAL W included in the software collection "Phylogeny Programs" (available from http://evolution.genetics.washington.edu/phylip/software. html, see Thompson, D. J., et al., *Nucleic Acids Res.*, 22, 4673–4680 (1994)). The phylogenetic tree can be prepared also by a generally available software (e.g., Tree View, Tree drawing software for Apple Machintosh: by Roderic D., Page 1995, Institute of Biomedical and Life Sciences, University of Glasgow, UK). Specifically, results obtained by computation on CLUSTAL W can be output as PHLYP format data, and they can be processed by Tree View. PHLYP (Felsenstein J. (1995) Phylogenetic inference package, version 3.5.7., Department of Genetics, University of Washington, Seatle Wash., USA) is also included in the aforementioned Phylogeny Programs.

[5] Other Biochemical and Physiological Characteristics (1) Quinone Type and GC Content of DNA The quinone type was ubiquinone-10 for all of the strains P528, S877, S1009, S1019 and S1023, and the GC content of DNA was 56.5%, 52.3%, 52.3%, 51.9%, and 52.9%, respectively.

(2) Acid Production

The multiple sequence alignment and evolution distance calculation can be performed by, for example, using a commercially available software such as CLUSTAL W included in the software collection "Phylogeny Programs". These programs are publically available from the Department of Genetics, University of Washington, Seattle, Wash., USA at their website: evolution.genetics.washington.edu/phylip/software.html. See also Thompson, D. J., et al. Nucleic Acids Res. 22, 4673–4680 (1994).

The phylogenetic tree can be prepared also by a generally available software (e.g., Tree View, Tree drawing software for Apple Macintosh: by Roderic. D., Page 1995, Institute of Biomedical and Life Sciences, University of Glasgow, UK). Specifically, results obtained by computation on CLUSTAL W can be output as PHLYP format data, and they can be processed by Tree View. PHLYP (Felsenstein, J. (1995) Phylogenetic inference package, version 3.5.7., Department of Genetics, University of Washington, Seattle, Wash., USA) is also included in the aforementioned Phylogeny Programs.

(6) Production of Acetic Acid and Consumption of Ethanol

When cultured in a medium containing glucose as a carbon source, the strains showed weak acetic acid productivity. The strains did not show significant ethanol consumption, and the strain P528 showed ethanol production.

[6] Phenotypic Comparison of Microorganisms of the Present Invention and Other Acetic Acid Bacteria The results of phenotypic comparison of the strains P528, S877, S1009, S1019 and S1023 and previously reported known acetic acid bacteria, *Asaia bogorensis, Acetobacter aceti, Gluconobacter oxydans, Gluconacetobacter liquefaciens,* and *Acidomonas methanolica* (The Congress of the Japan Society for Bioscience, Biotechnology, and Agrochemistry, 1999, Lecture Abstracts, p. and p. 66) are shown in Table 9. *Asaia bogorensis* is a microorganism belonging to a new genus (gen. nov.), and a new species (sp. nov.) reported in the meeting by Yamada et al. As for the strains P528, S877, S1009, S1019 and S1023, acetic acid production, ethanol production, DNA nucleotide composition, and major quinone were determined as described in Examples 5 and 6. The other characteristics are determined by the method of Asai et al. (Asai, T. et al., *J. Gen. Appl. Microbiol.*, 10 (2), p. 95, 1964).

TABLE 9

| | S-877, S-1009, S-1019, S-1023 | P-528 | Asaia | Acetobacter | Gluconobacter | Gluconoacetobacter | |
|---|---|---|---|---|---|---|---|
| Motility | − | − | +/− | +/− | +/− | +/− | − |
| Production of acetic acid from ethanol | W | W | − | + | + | + | + |
| Production of acetic acid from glucose | − | + | nd | − | nd | nd | |
| Oxidation of acetic acid | − | W | + | + | − | +/− | + |
| Oxidation of lactic acid | + | + | + | + | − | +/− | − |
| Growth | | | | | | | |
| Mannitol agar medium | + | + | + | t/− | + | +/− | − |
| Glutamic acid agar medium (1%) | − | + | + | +/− | − | +/− | − |
| Glutamic acid agar medium (7%) | + | + | nd | + | − | − | nd |
| Growth with 30% glucose | + | + | nd | − | − | +/− | − |
| Acid production | | | | | | | |
| From mannitol | + | + | + | + | +/− | − | |
| From sorbitoi | + | + | + | | | | |
| From glycerol | + | + | + | + | − | | |
| From ethanol | − | W/− | + | + | + | + | |
| DNA base composition (mol % G + C) | 52–53 | 56.5 | 59–61 | 53–63 | 56–64 | 55–66 | 63–66 |
| Major quinone | UQ-10 | UQ-10 | UQ-10 | UQ-9 | UQ-10 | UQ-10 | UQ-10 | nd: Not determined,
W: Weak

As shown in Table 9, the strain P528 resembles *Asaia bogorensis*, but it is different from *Asaia bogorensis* in that the strain showed acetic acid production from ethanol though it was weak and that GC content in a nucleotide composition of DNA is 56.5 which is significantly lower than that of *Asaia bogorensis* (59–61). The strains S877, S1009, S1019 and S1023 were different from the other acetic acid bacteria in that their acetic acid production from ethanol was weak, they could grow in the presence of 30% glucose, and they did not show acid production from ethanol.

Based on the above results, the strain P528 was identified as a new species belonging to the genus Asaia, and provisionally designated as *Asaia ethanolifaciens* sp. nov. The strains S877, S1009, S1019 and S1023 all were identified as a new species belonging to a new genus, and provisionally designated as *Zucharibacter floricola* gen. nov., sp. nov.

<2> Production Method of Xylitol and D-xylulose

Xylitol and/or D-xylulose can be produced by culturing a microorganism having an ability to produce xylitol or D-xylulose from glucose in a suitable medium so that xylitol or D-xylulose or the both should accumulate in the medium, and collecting xylitol and/or D-xylulose from the medium.

While the microorganism is not particularly limited so long as it has the ability to produce xylitol or D-xylulose from glucose, specific examples thereof include the aforementioned strains P528, S877, S1009, S1019 and S1023. Those microorganisms of the same species or belonging to the same genus as the aforementioned strains and having the ability to produce xylitol or D-xylulose from glucose can also be used for the present invention. Examples of such microorganisms include, for example, those belonging to the family Acetobacteracea, which has a 16S rRNA gene comprising a nucleotide sequence of SEQ ID NO: 1 or a nucleotide sequence equivalent to the nucleotide sequence from the viewpoint of molecular taxonomy based on the 16S rRNA sequence, or a nucleotide sequence of SEQ ID NO: 2 or a nucleotide sequence equivalent to the nucleotide sequence from the viewpoint of molecular taxonomy based on the 16S rRNA sequence, and has an ability to produce xylitol or D-xylulose from glucose. Specifically, those belonging to the genus Asaia or the genus Zucharibacter, more specifically strains of *Asaia ethanolifaciens* or *Zucharibacter floricola* can be mentioned.

The target product produced by the method of the present invention may be one of xylitol or D-xylulose, or both of them.

According to the present invention, any of mutant strains obtained from microbial strains having an ability to produce xylitol or D-xylulose from glucose by UV exposure, N-methyl-N'-nitro-N-nitrosoguanidine (NTG) treatment, ethyl methanesulfonate (EMS) treatment, nitrous acid treatment, acridine treatment and the like, or genetic recombinant strains and the like obtained by cell fusion or genetic engineering techniques such as genetic recombination can also be used.

The medium for culturing the aforementioned microorganisms may be a usual medium containing usual carbon source, nitrogen source, inorganic ions, as well as organic nutrients as required. While the microorganisms of the present invention grow under high osmotic stress condition, they may also grow under normal osmotic condition as the case may be. For example, the strain P528 grows under normal osmotic condition.

As the carbon source, carbohydrates such as glucose, alcohols such as glycerol, organic acids and the like can be suitably used. In view of the preference observed in the known methods for the production of xylitol, for example, the method for producing xylitol from pentitols such as D-xylose or D-arabitol, preferred are hexoses such as fructose and sucrose, disaccharides such as sucrose and lactose, and polysaccharides such as starch. These materials are used as a main carbon source in the medium in an amount of 10–60%, preferably 20–50%. These carbon sources may be added to the medium at a time, or in parts according to the cultivation time course.

As the nitrogen source, ammonia gas, aqueous ammonia, ammonium salts and the like are used. As the inorganic ions, magnesium ions, phosphate ions, potassium ions, iron ions, manganese ions and the like are used as required. As the organic nutrient, vitamins, amino acids and materials containing them such as lever extract, yeast extract, malt extract, peptone, meat extract, corn steep liquor, casein decomposition product and the like are used as required.

The culture conditions are also not particularly limited. However, the microorganisms may be cultured at limited pH and temperature selected within a pH range of 5–8 and temperature range of 25–40° C. The cultivation is performed under an aerobic condition by, for example, stirring or shaking for aeration. As for the culture period, the microorganisms are desirably cultured until the main carbon source is consumed, i.e., usually for 3–8 days.

Xylitol and/or D-xylulose produced in the medium during such cultivation as described above is separated and collected from the culture in a conventional manner. Specifically, for example, after the solid matter is removed from the culture by centrifugation, filtration or the like, the residual solution can be decolorized and desalted by using activated carbon, ion-exchange resin or the like, and xylitol and/or D-xylulose can be crystallized from the solution. The procedures of the separation and the collection of xylitol and/or D-xylulose from culture are easier than the separation from plant material hydrolysate because of lower content of impurities.

The produced D-xylulose can be converted into xylitol by hydrogenation, which can be performed in a known manner.

<3> Production Method of Ethanol

Ethanol can be produced by culturing the microbial strain P528 (FERM BP-6751) in a medium containing glucose so that ethanol should accumulate in the medium, and collecting ethanol from the medium. Other than the strain P528, microorganisms having 16S rRNA gene comprising a nucleotide sequence of SEQ ID NO: 1 or a nucleotide sequence equivalent to the nucleotide sequence from the viewpoint of molecular taxonomy based on the 16S rRNA sequence, and has an ability to produce ethanol from glucose, or mutant strains thereof can similarly be used for the production of ethanol.

The medium and culture conditions can be similar to those explained above for the method for producing xylitol and D-xylulose. Ethanol produced in the medium can be concentrated and purified in such a manner as used in usual ethanol fermentation.

BEST MODE FOR CARRYING OUT THE INVENTION

The present invention will be explained more specifically with reference to the following examples. However, the present invention is not limited to these examples.

In the examples, the produced xylitol and D-xylulose were analyzed by high performance liquid chromatography (HPLC) under the following conditions.

Column: Shodex SC1211 (product of Showa Denko)

Mobile phase: 50% acetonitrile/50% 50 ppm aqueous solution of Ca-EDTA

Flow rate: 0.8 ml/minute

Temperature: 60° C

Detection: RI detector

EXAMPLE 1

Isolation of Microorganisms Producing Xylitol or D-xylulose

First, osmophilic microorganisms were collected from nature by enrichment culture. A medium containing 20% D-glucose, 1% yeast extract (Difco), and 0.1% urea was introduced into test tubes in an amount of 4 ml each, and sterilized at 120° C. for 20 minutes. Soil samples collected from various locations were inoculated to the medium, and cultured at 30° C. for 4 to 7 days with shaking. When bacterial growth was observed, the culture was plated on an agar plate having the same composition, and incubated at 30° C. for 1 to 3 days. Then, formed colonies were picked up.

Then, about 3000 strains of osmophilic bacteria obtained as described above were cultured in a medium containing 20% (w/v) D-glucose, 0. 1% urea, and 0.5% yeast extract at 30° C. for 5 days, and the medium was analyzed by HPLC to screen for a strain having the xylitol or D-xylulose producing ability. As a result, five bacterial strains separated from soil collected from the back of Tama river, Kawasaki-shi, Kanagawa-ken, were found to have the ability to produce xylitol from glucose. These strains were each designated as strains P528, S877, S1009, S1019 and S1023. These five strains were assigned private numbers of AJ14757, AJ14758, AJ14759, AJ14760, and AJ14761 in this order, and have been deposited since Jun. 18, 1998 at the National Institute of Bioscience and Human-Technology, Agency of Industrial Science and Technology (zip code: 305-8566, 1-3 Higashi 1-Chome, Tsukuba-shi, Ibaraki-ken, Japan), as deposition numbers of FERM P-16848, FERM P-16849, FERM P-16850, FERM P-16851, and FERM P-16852 in this order, and transferred from the original deposition to international deposition based on Budapest Treaty on Jun. 14, 1999, and has been deposited as deposition numbers of FERM BP-6751, FERM BP-6752, FERM BP-6753, FERM BP-6754, and FERM BP-6755.

EXAMPLE 2

Production of Xylitol and D-xylulose from Glucose

A medium containing 0.5% yeast extract (Difco), and 0.1% urea (pH 6.0) was introduced into a 500 ml Sakaguchi flask in an amount of 50 ml, and sterilized by heating at 120° C. for 20 minutes. Separately sterilized glucose was added to this medium in such an amount that the medium should contain 20% (w/v) glucose. The strains P528, S877, S1009, S1019 and S1023 were each inoculated to this medium, and cultured at 30° C. for 5 days with shaking. Then, after the bacterial cells were removed by centrifugation, xylitol and D-xylulose formed in the medium were mesured by HPLC. The results are shown in Table 10.

TABLE 10

| | Production amount of xylitol and D-xylulose | |
|---|---|---|
| Strain | Concentration of produced xylitol (g/l) | Concentration of produced D-xylulose (g/l) |
| P528 | 5.3 | 3.3 |
| S877 | 1.9 | 9.7 |
| S1009 | 1.6 | 9.0 |
| S1010 | 1.7 | 9.2 |
| S1023 | 1.5 | 5.0 |

EXAMPLE 3

Molecular Taxonomic Analysis of Strains P528, S877, S1009, S1019 and S1023

The strains P528 and S877 were analyzed from the viewpoint of molecular taxonomy by nucleotide sequence analysis of 16S rRNA in a conventional manner.

A bacterial cell suspension of each strain was treated with protease at 60° C. for 20 minutes, then heated in boiling water for 5 minutes, and centrifuged. The obtained supernatant was directly used as template for PCR.

Using universal primers corresponding to the positions 8–27 and 1492–1510 of the 16S rRNA of *E. coli* (SEQ ID NOS: 6 and 7), 30 cycles of PCR was performed in a conventional manner, and the product was collected by PEG precipitation. The PCR product was directly sequenced by fluorescence cycle sequencing, and the reaction product was analyzed by a DNA sequencer (Pharmacia). The determined nucleotide sequences are shown in SEQ ID NO: 1 (strain P528) and SEQ ID NO: 2 (strain S877). Any sequence corresponding to these nucleotide sequences was not found in databases. The bacterial group having the closest nucleotide sequences of the 16S rRNA gene for each strain was bacteria belonging to the genus Gluconobacter and the genus Acetobacter.

The obtained nucleotide sequence data were processed by GENETYX (Software Development, Tokyo), and multiple alignment and evolution distance calculation were performed by CLUSTAL W for the obtained sequences and analogous sequences available from databases (16S rRNA gene sequences of 13 kinds of acetic acid bacteria currently considered valid names). The obtained PHYLIP format data were read and processed by Tree View to prepare a molecular phylogenetic tree. The result is shown in FIG. 1. The alignment of 16S rRNA of the xylitol producing bacteria is shown in FIGS. 2 and 3. The aforementioned 13 kinds of acetic acid bacteria are mentioned below.

*Gluconobacter asaii*
*Gluconobacter cerinus*
*Gluconobacter frateurii*
*Gluconobacter oxydans* subsp. *oxydans*
*Acetobacter aceti*
*Acetobacter pasteurianus*
*Acetobacter methanolicus*
*Gluconobacter europaeus*
*Gluconobacter xylinus* subsp. *xylinus*
*Gluconobacter intermedicus*
*Gluconobacter hansenii*
*Gluconobacter liquefaciens*
*Gluconobacter diazotrophicus*
*Rhodophila globiformis*

As a result, known strains exhibiting a close evolution distance with respect to the strain P528 were *Gluconobacter intermedicus*, *Gluconobacter liquefaciens*, *Acetobacter aceti*, *Acetobacter methanolicus* and *Acetobacter pasteurianus*, whose evolution distance was 0.0345, 0.0359, 0.0403, 0.0419 and 0.0499, and homology of the 16S rRNA gene was 96.5%, 96.3%, 96.0%, 95.9% and 95.1%, respectively. Further, known strains exhibiting a close evolution distance with respect to the strain S877 were *Gluconobacter cerinus* and *Gluconobacter oxydans*, whose evolution distance was 0.0622 and 0.0629, and homology of the 16S rRNA gene was 94.0% and 93.9%, respectively. While the strain P528 is included in the cluster of the genus Acetobacter, it was far away from three strains of the known species, and hence considered a new species. *Acetobacter methanolicus* has also been reported to belong to another genus (genus Acidomonas). If *Acetobacter methanolicus* is considered to belong to another genus, the strain P528 may belong to a new genus, since the strain is located outside the cluster of the genus Acetobacter.

On the other hand, the strain S877 is located outside the cluster of the genus Gluconobacter, and far away from any known species belonging to the genus Gluconobacter. The evolution distance from the strain S877 to the closest strain (*Gluconobacter cerinus*) is 0.066, and this value is significantly larger than the distance between the genus Gluconobacter and the genus Acetobacter (0.044). Therefore, it is reasonable to consider that this strain belongs to a new genus.

When partial nucleotide sequences of the 16S rRNA of the strains S1009, S1019 and S1023 were determined (SEQ ID NOS: 3 to 5, respectively), they showed substantially the same sequence as that of the strain S877, and hence they were found to be of the same species.

From the above molecular taxonomic analysis and the phenotypes shown in Table 9, the strain P528 was identified as a new species belonging to the genus Asaia, and provisionally designated as *Asaia ethanolifaciens* sp. nov. The strains S877, S1009, S1019 and S1023 strain were all identified as a microorganism of a new species belonging to a new genus, and provisionally designated as *Zucharibacter floricola* gen. nov., sp. nov.

EXAMPLE 4

Production of Xylitol and D-xylulose from Glucose

A medium containing 0.2% ammonium acetate, 0.3% potassium dihydrogenphosphate, 0.05% magnesium sulfate heptahydrate, 0.5% yeast extract (Difco), and 4% calcium carbonate was introduced into a 500 ml Sakaguchi flask in an amount of 50 ml, and sterilized by heating at 120° C. for 20 minutes. Separately sterilized glucose was added to the medium in such an amount that the medium should contain 20% (w/v) glucose. The strain P528 was inoculated to this medium, and cultured at 30° C. for 4 days with shaking. Then, after the bacterial cells were removed by centrifugation, xylitol and D-xylulose formed in the medium were mesured by HPLC. As a result, it was found that 6.4 g/L of xylitol and 17.5 g/L of D-xylulose was formed.

EXAMPLE 5

Biochemical and Physiological Characteristics of Strains P528, S877, S1009, S1019 and S1023

(1) Analysis of Quinone and GC Content of DNA

Quinone and GC content of DNA of the aforementioned strains were analyzed by high performance liquid chromatography (HPLC) in a usual manner (see Saikingaku Gijutsu Sosho (Library of Techniques in Bacteriology), Vol. 8 "Method for Microbial Identification Following New Taxonomy", pp.61–73, pp.88–97, Saikon Shuppan, Japan). The results are shown in Table 11.

TABLE 11

| | Quinone type and GC content of DNA | | | | |
|---|---|---|---|---|---|
| Strain | P528 | S877 | S1009 | S1019 | S1023 |
| Quinone | UQ-10 | UQ-10 | UQ-10 | UQ-10 | UQ-10 |
| GC (%) | 56.5 | 52.3 | 52.3 | 51.9 | 52.9 |

UQ: Ubiquinone (2) Acid Production from Various Carbon Sources

The aforementioned strains were each cultured in a medium containing one of various carbon sources (1%), and presence of formed acid was determined. The strains were pre-cultured in the YPG medium at 28° C. for one day, and the bacterial cells were washed with 0.5% yeast extract solution, inoculated to the YPC medium, and cultured at 28° C. for 4 to 7 days with shaking. Then, production of acid was determined by color variation (purplish red to yellow) of pH indicator in the medium.

The YPG medium was prepared as follows. A medium containing 1% yeast extract (Difco), and 1% peptone was sterilized by heating at 120° C. for 20 minutes. To this medium, separately sterilized D-glucose was added in such an amount that the medium should contain 7% D-glucose.

The YPC medium was prepared as follows. A medium containing 0.5% yeast extract (Difco), 0.012% bromocresol purple, and 1% of one of various carbon sources was sterilized by heating at 120° C. for 20 minutes.

The results are shown in Table 12.

TABLE 12

Acid formation from various carbon sources

| Strain | P528 | S877 | S1009 | S1019 | S1023 |
|---|---|---|---|---|---|
| Xylose | + | − | − | − | − |
| Arabinose | + | − | − | − | − |
| Glucose | + | + | + | + | + |
| Galactose | + | − | − | − | − |
| Mannose | + | − | + | + | + |
| Fructose | + | + | − | − | − |
| Sorbase | ± | − | − | − | − |
| Sucrose | ± | + | + | + | + |
| Maltose | − | − | − | − | − |
| Rhamnose | + | − | − | − | − |
| Glycerol | ± | − | − | − | − |
| Mannitol | ± | + | + | + | + |
| Sorbitol | ± | − | − | − | − |
| Lactose | + | − | − | − | − |
| Starch | − | − | − | − | − |
| Ethanol | − | − | − | − | − |

+: Presence of acid production,
±: weak acid production,
−: no acid production (3) Influence of NaCl Addition on Growth Influence of NaCl addition on growth of the aforementioned strains was examined by culture in the YPM medium. The aforementioned strains and *Acetobacter aceti* strain NCIB 8621 as a control were pre-incubated in the aforementioned YPG medium at 28° C. for one day, and the bacterial cells were washed with the YPG medium not added with D-glucose, and suspended in the YPG medium not added with D-glucose. The obtained bacterial suspension was inoculated (1.6% v/v) to YPM medium added with NaCl at one of various concentrations, and cultured at 28° C. for two days with shaking. Then, turbidity of the medium was measured by a spectrophotometer ANA-75A from Tokyo Koden (OD 660 nm) to determine the growth.

The YPM medium was prepared as follows. A medium containing 1% yeast extract (Difco), 1% peptone, and 1% mannitol was sterilized by heating at 120° C. for 20 minutes.

Figure 4:
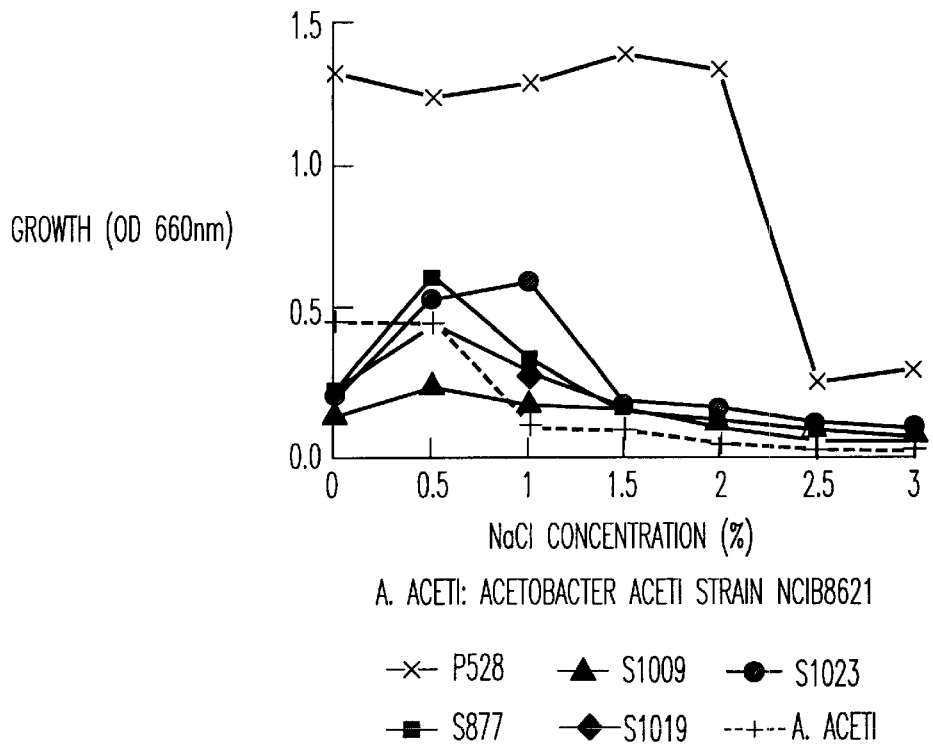
FIG. 4 is a graph representing influence of NaCl addition on growth of microorganisms of the present invention.

The results are shown in FIG. 4. The strain P528 showed active growth in a medium added with up to 2% of NaCl, i.e., showed NaCl resistance.

(4) Consumption of Acetic Acid and Lactic Acid

The aforementioned strains were cultured in the YG medium added with acetic acid or lactic acid to examine consumption of acetic acid and lactic acid.

The aforementioned strains and *Acetobacter aceti* strain NCIB 8621 as a control were pre-cultured in the aforementioned YPG medium at 28° C. for one day with shaking. The obtained pre-medium was inoculated (1.6%, v/v) to YG medium added with 1% acetic acid or lactic acid, and incubated at 28° C. for seven days. The consumption of acetic acid and lactic acid was examined by time course sampling of the medium. The measurement of acetic acid and lactic acid was performed by HPLC under the following conditions.

Column: ULTTRON PS-80 (product of Shinwa Kagaku Kogyo)
Mobile phase: Perchloric acid solution (pH 2.1)
Flow rate: 0.9 ml/minute
Temperature: 60° C.
Detection: UV detector (210 nm)

The YG medium added with acetic acid or lactic acid was prepared as follows. A medium containing 1% yeast extract (Difco), and 1% acetic acid or lactic acid was adjusted to pH 6.0, and sterilized by heating at 120° C. for 20 minutes. Separately sterilized D-glucose was added to the medium in such an amount that the medium should contain 7% D-glucose.

The results are shown in Table 13 (the data were represented in consumed amount (%)). The strains P528, S877, S1009, S1019 and S1023 all showed lactic acid decomposition ability, whereas they showed weak or substantially no acetic acid decomposition ability.

TABLE 13

Consumption of acetic acid and lactic acid

| Strain | P528 | S877 | S1009 | S1019 | S1023 | A. aceti |
|---|---|---|---|---|---|---|
| Acetic acid (%) | 37.8 | 100.0 | 88.6 | 100.0 | 96.6 | 7.7 |
| Lactic acid (%) | 0.0 | 4.7 | 29.7 | 30.7 | 24.3 | 0.0 |

A. aceti: Acetobacter aceti strain NCIB8621

(5) Influence of Acetic acid or Ethanol Addition on Growth

Influence of addition of acetic acid on growth of the aforementioned strains was examined in the YG medium added with acetic acid. Influence of addition of ethanol on growth of the aforementioned strains was also examined in the YPG medium added with ethanol.

The aforementioned strains were each pre-cultured in the foregoing YPG medium at 28° C. for one day, and each medium was inoculated (1.6% v/v) to the YG medium added with lactic acid at one of various concentrations, and the YPG medium added with ethanol at one of various concentrations, and incubated at 28° C. for ten days with shaking. Then, turbidity of the medium was measured by a spectrophotometer ANA-75A from Tokyo Koden (OD 660 nm) to determine the growth.

All of the strains P528, S877, S1009, S1019 and S1023 showed active growth in the medium added with up to 1% acetic acid or 3% ethanol. All of the strains did not grow in the medium added with 4% or more of acetic acid or 5% or more of ethanol.

(6) Production of Acetic Acid and Consumption of Ethanol

The aforementioned strains were cultured in the YPG medium added with ethanol to examine production of acetic acid and consumption of ethanol. The aforementioned strains and *Acetobacter aceti* strain NCIB 8621 as a control were pre-cultured in the aforementioned YPG medium at 28° C. for two days. Each medium was inoculated (1%, v/v) to the YPG medium added with 1% ethanol and incubated at 28° C. The concentrations of acetic acid and ethanol in the medium were examined by time course sampling of the medium. The measurement of acetic acid and ethanol concentrations was performed by using F-kit (Roche Diagnostics).

Figure 5:
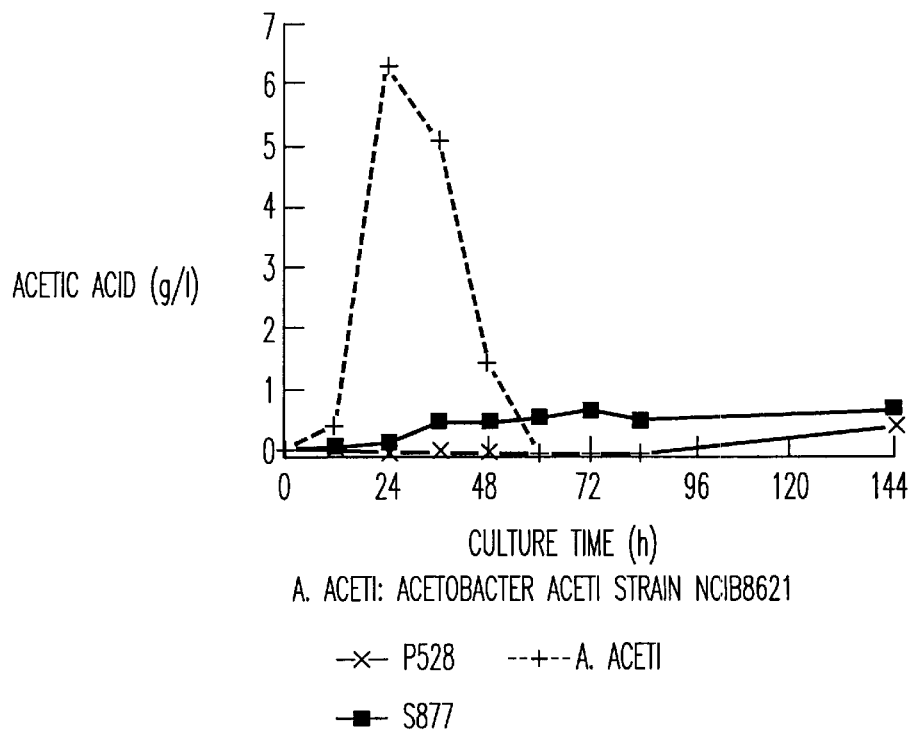
FIG. 5 is a graph representing production of acetic acid when the strains P528 and S877 are cultured in a medium added with ethanol.
Figure 6:
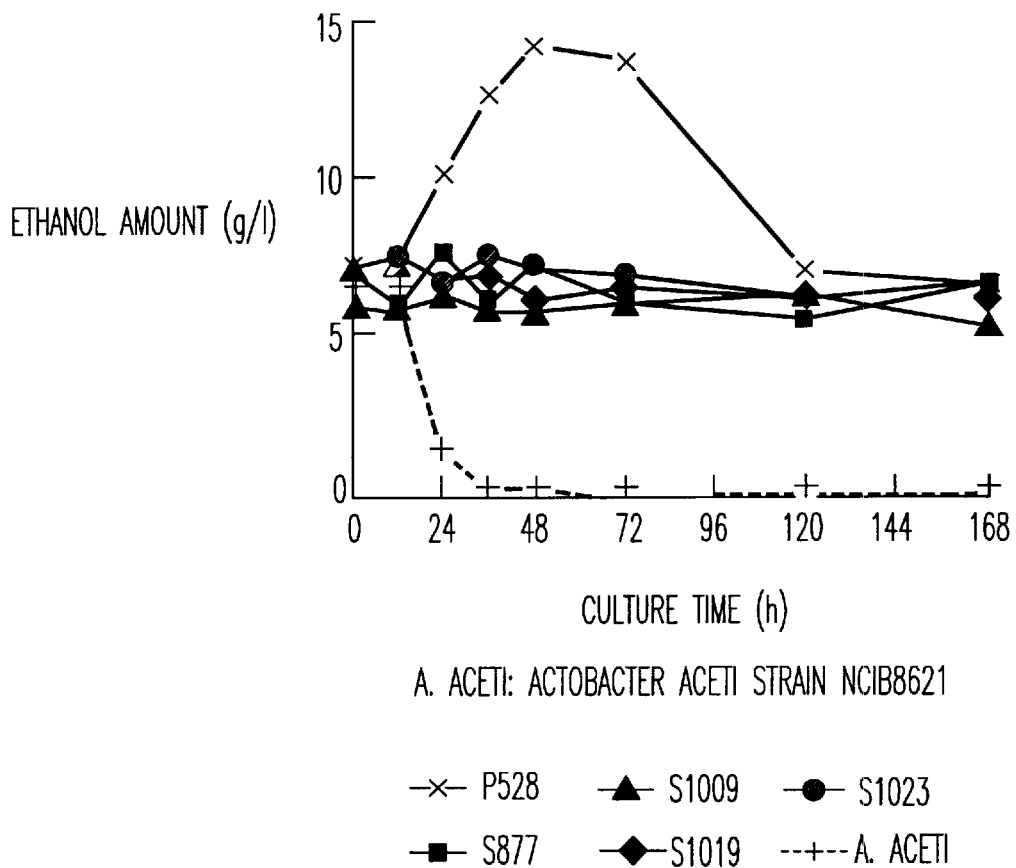
FIG. 6 is a graph representing consumption or production of ethanol when the strains P528 and S877 are cultured in a medium added with ethanol.

The results are shown in FIGS. 5 and 6. All of the strains P528, S877, S1009, S1019 and S1023 showed weaker acetic acid productivity compared with the control bacteria, *Acetobacter aceti* strain NCIB 8621 (the figure indicates the data only for the strains P528 and S877). Further, strains S877, S1009, S1019 and S1023 did not show ethanol consumption in contrast to the control bacteria, *Acetobacter aceti* strain NCIB 8621. The strain P528 showed, to the contrary, showed increase of ethanol amount.

EXAMPLE 6
Production of Ethanol by Strain P528

Figure 7:
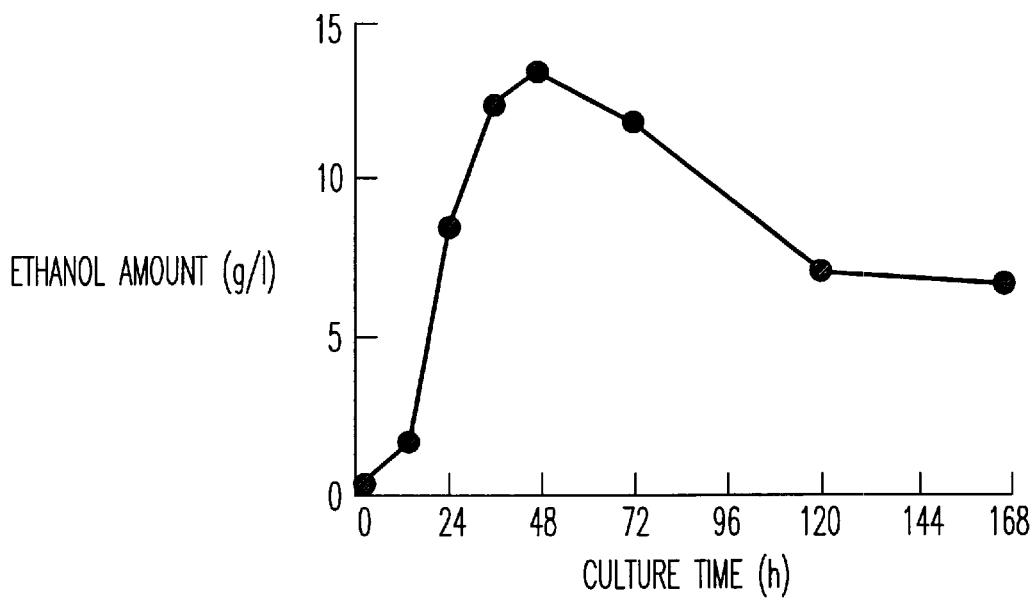
FIG. 7 is a graph representing ethanol production by the strain P528.

The strain P528 was cultured by using the YPG medium in a manner similar to that mentioned above, and ethanol concentration in the medium was measured over time. The results are shown in FIG. 7. The strain P528 showed ethanol productivity.

What is claimed is:

1. An isolated microbial strain, P528 (FERM BP-6751), having an ability to produce xylitol or D-xylulose from glucose.

2. An isolated microbial strain, S877 (FERM BP-6752), having an ability to produce xylitol or D-xylulose from glucose.

3. An isolated microbial strain, S1009 (FERM BP-6753), having an ability to produce xylitol or D-xylulose from glucose.

4. An isolated microbial strain, S1019 (FERM BP-6754), having an ability to produce xylitol or D-xylulose from glucose.

5. An isolated microbial strain, S1023 (FERM BP-6755), having an ability to produce xylitol or D-xylulose from glucose.

6. A method for producing xylitol or D-xylulose, which comprises:

culturing a strain selected from the group consisting of strain P528 (FERM BP-6751), S877 (FERM BP-6752), S1009 (FERM BP-6753), S1019 (FERM BP-6754), and S1023 (FERM BP-6755) in a suitable medium to accumulate xylitol or D-xylulose in the medium, and collecting xylitol or D-xylulose from the medium.

7. A method for producing ethanol, which comprises:

culturing an isolated microbial strain, P528 (FERM BP-675 1), in a suitable medium to accumulate ethanol in the medium, and collecting ethanol from the medium.

* * * * *